United States Patent [19]

Rakoczi et al.

[11] Patent Number: 4,730,037

[45] Date of Patent: Mar. 8, 1988

[54] PROCESS FOR THE APPLICATION OF IR SPECTROSCOPY FOR MODULATION AND MONITORING OF DIAZONIUM ION CONCENTRATION

[75] Inventors: Ferenc Rakoczi, Zurich, Switzerland; Rüdiger Oxenius, Rheinfelden, Fed. Rep. of Germany

[73] Assignee: Ciba-Geigy Corporation, Ardsley, N.Y.

[21] Appl. No.: 899,149

[22] Filed: Aug. 22, 1986

[30] Foreign Application Priority Data

Aug. 22, 1985 [CH] Switzerland .................... 3604/85

[51] Int. Cl.$^4$ .................. C07C 113/04; C09D 29/00; G01N 21/34; G05B 11/00
[52] U.S. Cl. ......................... 534/565; 422/62; 422/68; 422/108; 422/110; 534/558; 534/560; 534/565; 534/579; 534/581; 534/582
[58] Field of Search .............. 534/565, 579, 558, 581, 534/582, 560; 422/62, 68, 108, 110

[56] References Cited

U.S. PATENT DOCUMENTS

| | | | |
|---|---|---|---|
| 3,117,954 | 1/1964 | Hupfer | 534/565 |
| 3,423,391 | 1/1969 | Kindler et al. | 534/565 |
| 4,159,264 | 6/1979 | Hamilton et al. | 534/565 |
| 4,190,578 | 2/1980 | Hamilton et al. | 534/565 |
| 4,234,478 | 11/1980 | Atherton et al. | 534/565 X |
| 4,268,437 | 5/1981 | Behringer et al. | 534/565 |
| 4,439,361 | 3/1984 | Karrenbauer et al. | 534/565 |

FOREIGN PATENT DOCUMENTS

| | | | |
|---|---|---|---|
| 191399 | 8/1957 | Austria | 534/565 |
| 2617953 | 11/1976 | Fed. Rep. of Germany | 534/565 |
| 618456 | 7/1980 | Switzerland | 534/565 |
| 226229 | 1/1969 | U.S.S.R. | 534/565 |
| 654846 | 3/1986 | Switzerland | 534/565 |
| 1004360 | 3/1983 | U.S.S.R. | 534/565 |
| 1121274 | 10/1984 | U.S.S.R. | 534/565 |
| 2129434 | 5/1984 | United Kingdom | 534/565 |

OTHER PUBLICATIONS

Bailey, Control Engineering, Jan. 1982, pp. 78–80.
Reed et al, Chemical Abstracts, vol. 88, #58042y (1978).
Hesse et al., *Spektroskopische Methoden in der Organischen Chemie*, Georg Thieme Verlag 1984, p. 53.

*Primary Examiner*—Floyd D. Higel
*Attorney, Agent, or Firm*—Wenderoth, Lind & Ponack

[57] ABSTRACT

The invention relates to a method of determining and controlling the diazonium ion concentration in diazotization solutions and/or in azo coupling reactions, which comprises determining said diazonium ion concentration by means of IR spectroscopy from the intensity of the N≡N stretching frequency.

The method is extremely selective and virtually trouble-free and permits the simultaneous determination of the concentration of different diazonium salts in mixtures.

7 Claims, No Drawings

PROCESS FOR THE APPLICATION OF IR SPECTROSCOPY FOR MODULATION AND MONITORING OF DIAZONIUM ION CONCENTRATION

The present invention relates to a method of determining the diazonium ion concentration in diazotisation solutions and/or in azo coupling reactions by means of infra-red (IR) spectroscopy.

In recent years, increasing efforts have been made to automate dye manufacture both with respect to the actual preparatory process itself and to the working up. As regards the process for the preparation of one of the most important classes of dye, namely azo dyes, there is still a need for simple methods of monitoring the two basic synthesis steps, i.e. the diazotisation and coupling reactions. Common to both reactions is a change in the diazonium ion concentration during the reaction course. It should therefore be possible to control diazotisation as well as coupling by determining the diazonium ion concentration.

It has now been found that such control is possible in simple and elegant manner by infrared spectroscopic analysis of the respective reactive mixtures. The $-N_2+$ group of the diazonium salts is detected in the infra-red spectrum by a strong band in a wave number range from $\nu=2150$ to $2350$ cm$^{-1}$, the intensity of which band is a function of the diazonium ion concentration.

Accordingly, the present invention relates to a method of determining and controlling the diazonium ion concentration in diazotisation solutions and/or in azo coupling reactions, which process comprises determining said diazonium ion concentration by IR spectroscopy from the intensity of the $N\equiv N$ stretching frequency.

The IR spectroscopic measurement can be made by taking samples during the diazotisation and coupling reactions at specific intervals and examining them spectroscopically in the respective wave number range, or by passing small amounts of the diazotisation solution or coupling suspension over a by-pass continuously in a flow cell and continuously recording the intensity of the $N\equiv N$ stretching frequency. The continuous measurement is preferred, as it permits the reactant streams to be influenced immediately, even when there are insignificant changes in concentration. If, as in azo coupling is often the case, the reaction mixture is in the form of a suspension, it is advantageous to effect filtration before the IR measurement, for example by subjecting a partial stream of the suspension to continuous clarifying filtration and analysing the filtrate by IR spectroscopy. In this manner the process is always carried out in homogeneous phase and the result cannot be influenced by the solids content. Filtration is conveniently effected by means of a membrane separating method, e.g. by microfiltration, ultrafiltration or hyperfiltration.

During the diazotisation, the flow of nitrite or amine will conveniently be controlled via the intensity of the $N\equiv N$ stretching frequency, i.e. whenever the signal of the $N\equiv N$ stretching frequency has reached a nominal value determined by prior experimentation, the flow of nitrite or amine is corrected accordingly. By this means it is possible to avoid an overaddition of nitrite and also to control the concentration of nitrite during diazotisation such that undesirable secondary reactions do not occur.

The diazotisation will normally be carried out continuously or batchwise in a solution containing mineral acid. If diazotisation is effected batchwise, the amine will be suspended or dissolved, e.g. in aqueous hydrochloric acid, and then reacted with an aqueous nitrite solution, e.g. an aqueous solution of sodium nitrite. The reaction proceeds almost quantitatively.

In the preferred continuous method, the procedure is for example that the diazo component is diazotised continuously with sodium nitrite in a tube reactor. Simultaneously, the intensity of the $N\equiv N$ stretching frequency is measured with an IR spectrophotometer. The fluctuations in intensity measured with the IR spectrophotometer are processed by a process control computer which controls the reactant streams after comparison with the nominal value via a corresponding signal.

The method of this invention is susceptible of application to all diazotisable amines. It is preferred to carry out the method of determining and controlling the diazonium ion concentration in diazotisation solutions and/or during azo coupling reactions in the presence of a polar solvent, e.g. water, an alcohol such as methanol, ethanol, propanol, isopropanol or butanol, or a ketone such as methyl isopropyl ketone. It is particularly preferred to carry out the determination and control of the diazonium ion concentration in aqueous solution.

Examples of suitable diazo components are: aniline and derivatives thereof such as 4-nitroaniline, 3-nitroaniline, 2-chloro-4-nitroaniline, 4-chloro-2-nitroaniline, 2,6-dichloro-4-nitroaniline, 4-aminoacetanilide, 2,4-dinitroaniline, 4-chloroaniline, 2,4,5-trichloroaniline, 2,5-dimethoxyaniline, o-anisidine, p-anisidine, o-phenetidine, p-phenetidine, o-toluidine, p-toluidine, 4-nitro-2-aminoanisole, 2-nitro-4-aminoanisole, p-phenoxyaniline, or also 4-methylsulfonylaniline, 4-amino-2,4-dichlorobenzophenone, 4'-amino-2,4-dinitrobenzophenone, 2-nitroaniline, 2-chloro-4,6-dinitroaniline, 2,5-dichloroaniline, 3,3'-dichlorobenzidine, 5-nitro-2-aminoanisole, 3-nitro-4-aminotoluene, 2,4-dichloroaniline, 3-nitro-4-aminoanisole, 2-aminoanisole-4-sulfodiethylamide, 5-chloro-2-aminotoluene, 4-chloro-2-aminotoluene, 4-nitro-2-aminotoluene, 5-nitro-2-aminotoluene, 4-nitro-2-aminoanisole, 3,3'-dimethoxybenzidine, 3,3'-dimethoxy-6,6'-dichlorobenzidine, 2-amino-4-chlorophenol, 2-aminophenol-4-sulfamide, 2-aminophenol-5-sulfamide, 2-aminophenol-4-sulfomethylamide, 3-amino-4-hydroxyphenylmethylsulfone, 2-amino-5-nitrophenylmethylsulfone, 4-amino-3-nitrophenylmethylsulfone, 2-(N-methyl-N-cyclohexylsulfamoyl)aniline, 2-amino-4,2',4'-trichlorodiphenyl ether and 4-aminoazobenzene; α- or β-napthylamine, and derivatives thereof, such as 2-naphthylamine-6,8-disulfonic acid, 1-naphthylamine-3,6,8-trisulfonic acid, 4-naphthylamino-5-hydroxy-1,7-disulfonic acid or 2-naphthylamino-7-hydroxy-6-sulfonic acid.

Examples of heterocyclic amines are: 3-amino-1,2,4-triazole, 2-aminothiazole, benzthiazoles such as 2-aminobenzthiazole, 2-amino-4-chlorobenzthiazole, 2-amino-4-cyanobenzthiazole, 2-amino-4,6-dinitrobenzthiazole, 2-amino-4-methoxy-6-nitrobenzthiazole, 2-amino-6-methoxy-1,3-benzothiazole or aminobenztriazoles, which may also be appropriately substituted.

The solution of the diazonium salt may be kept in a storage vessel or, without being stored, reacted with a suitable coupling component to give the azo dye. The azo coupling can also be carried out continuously or batchwise. Continuous coupling is conveniently carried out in a tube reactor or multi-compartment reactor. Such a reactor may be provided at one or more sites with a sampling means. Sampling can in turn be effected at specific intervals or, preferably, continuously. The intensity of the N≡N stretching frequency is here employed as controlled variable for controlling the rate of addition of the diazo or coupling component; or, in other words, the ratio of diazo component to coupling component is controlled in this manner and, as required, freshly adjusted. Hence it is possible to achieve a virtually quantitative conversion of the starting materials to the desired azo dye. Secondary reactions can thus be reduced to a minimum and a standard type dye is obtained.

Depending on the diazo and coupling components, the azo coupling is carried out in an acid or basic reaction medium, with the optional addition of surfactants if it is desired to obtain a substantially finely particulate dye dispersion. In addition to the amines already mentioned as suitable diazo components, the following compounds may be cited as examples of suitable coupling components: N-substituted anilines, e.g. N,N-dimethylaniline, N,N-di-($\beta$-carbomethoxyethyl)aniline, N-($\gamma$-methoxypropyl)-3-acetylaminoaniline, N,N-di-($\beta$-hydroxyethyl)-2,5-dimethoxyaniline, N-ethyl-N-($\beta$-hydroxyethyl)aniline, N,N-di-($\beta$-hydroxyethyl)aniline; and also phenol and substituted phenols such as o-, m- and p-cresol, resorcinol, 4-phenylazo-1,3-dihydroxybenzene and 3-acetylaminophenol, naphthols such as 1- or 2-naphthol, 6-bromo-2-naphthol, 4-methoxy-1-naphthol and 2-naphthol-6-sulfonamide; as well as acylacetoarylamides, 2,6-dihydroxypyridines or 5-pyrazolones.

In principle, the intensity of the N≡N stretching frequency can be used for controlling the individual reactions, i.e. the diazotisation and coupling, as well as for monitoring both reactions.

The IR spectroscopic analysis is carried out with a commercially available IR spectrophotometer. Plates made of inorganic salts which are IR-permeable are normally used as window material, e.g. calcium fluoride plates. A compensating window is usually inserted into the reference path of rays of the spectrophotometer to compensate for the energy absorption and the losses in reflectance of the measuring cell. The processing of the intensity fluctuations measured in the N≡N stretching frequency range can be made direct on-line with the process control computer, which is this case controls the reactant streams.

It must be borne in mind that C—C triple bonds, the cyanide group and the isocyanate group absorb in the same wave number range as the diazonium group (q.v. "Spektroskopische Methoden in der organischen Chemie", Georg Thieme Verlag 1984, page 53). When using diazo components and coupling components which contain triple bonds or corresponding substituents, it must be established by prior experimentation whether the possibility exists—depending on the position of the bands—of monitoring their conversion by means of the method of this invention. In principle, however, the method described herein is exceedingly selective and substantially trouble-free, and furthermore permits the simultaneous monitoring of different diazonium salts—a feature which is advantageous when diazotising mixtures of amines.

The method of this invention is susceptible of application in particular to all amines which can be diazotised in acid aqueous medium and to all azo dyes which can be obtained by azo coupling.

In particular, the method of this invention can be used in continuous diazotisation and coupling reactions for the preparation of azo dyes. The preferred utility is as part of an on-line control of a computer-integrated, automated process for the preparation of azo dyes.

The invention is illustrated by the following Example in which percentages are by weight.

EXAMPLE (Diazotisation reaction)

A mixture of 4-aminoacetanilide and aniline (molar ratio 0.45:0.55) is diazotised in dilute hydrochloric acid with 4N aqueous sodium nitrite solution. The diazotisation is carried out at three different amine concentrations of 0.071, 0.142 and 0.284 mole/l. After complete conversion of the mixture of amines to the corresponding diazonium salts, the individual reaction mixtures are analysed by IR spectroscopy. This is done in each case by recording the N≡N stretching frequency in the wavelength range from 4 to 5 nm ($\leq$ a wavelength range of $\nu$=2000 to 2500 cm$^{-1}$). In the illustration, the absorption bands are superimposed. The transmission in percent (% T) is indicated as scale of ordinates. This corresponds to the percentage radiation which is absorbed by the sample at the respective wavelength. The comparison radiation serves as reference. The abscissa is calibrated in nm (wavelength $\lambda$). Band (a) corresponds to a total diazonium ion concentration of 0.07, band (b) corresponds to a concentration of both diazonium salts of altogether 0.28 mole/l, and band (c) corresponds to a concentration of altogether 0.28 mole/l, provided the diazotisation is quantitative. All three bands have a shoulder relative to the absorption peak at slightly shorter wavelength, caused by the N≡N stretching frequency of the diazotised aniline.

The bands show clearly the dependence of the concentration of the IR signal on the N≡N stretching frequency. In diazotisation reactions, the addition of amine or nitrile is controlled by means of the intensity of the IR signal as controlled variable.

The diazotisation reaction of the following amines is controlled by the same method: 2-chloro-4-nitroaniline, 4-chloro-2-nitroaniline, 3-amino-1,2,4-triazole.

What is claimed is:

1. A method of determining and controlling the diazonium ion concentration in diazotisation solutions or in azo coupling reactions, which comprises determining said diazonium ion concentration by means of IR spectroscopy from the intensity of the N≡N stretching frequency.

2. A method according to claim 1, wherein determination of the diazonium ion concentration is made continuously.

3. A method according to claim 1, which comprises filtering the reaction mixture beforehand if it is in the form of a suspension and analysing the filtrate by IR spectroscopy.

4. A method according to claim 1, which comprises controlling the addition of nitrite or amine during diazotisation or the ratio of diazo component to coupling component during the subsequent azo coupling reaction by using the value obtained by IR spectroscopy as controlled variable.

5. A process for the preparation of azo dyes with the aid of the method as claimed in claim 1.

6. A process for the continuous preparation of azo dyes with the aid of the process as claimed in claim 1.

7. The method as claimed in claim 1 as part of an on-line method of controlling a computer-integrated, automated process for the preparation of azo dyes.

* * * * *